US007651600B2

(12) United States Patent
Han et al.

(10) Patent No.: US 7,651,600 B2
(45) Date of Patent: Jan. 26, 2010

(54) ELECTROKINETIC CONCENTRATION DEVICE AND METHODS OF USE THEREOF

(75) Inventors: Jongyoon Han, Bedford, MA (US); Ying-Chih Wang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 428 days.

(21) Appl. No.: 11/338,885

(22) Filed: Jan. 25, 2006

(65) Prior Publication Data
US 2006/0180469 A1 Aug. 17, 2006

Related U.S. Application Data

(60) Provisional application No. 60/646,513, filed on Jan. 25, 2005.

(51) Int. Cl.
*G01N 27/26* (2006.01)
(52) U.S. Cl. ............ 204/601; 977/904; 977/924
(58) Field of Classification Search ........ 204/601; 977/904, 924
See application file for complete search history.

(56) References Cited

U.S. PATENT DOCUMENTS

| 5,374,834 | A * | 12/1994 | Geis et al. ........ 257/239 |
| 6,326,083 | B1 * | 12/2001 | Yang et al. ........ 428/429 |
| 6,399,389 | B1 * | 6/2002 | Parce et al. ........ 436/47 |
| 6,951,682 | B1 * | 10/2005 | Zebala ........ 428/312.2 |

OTHER PUBLICATIONS

Petersen et al., "Study of Interface Conductivity and Its Possible Applications" in Proceedings of the 8th International Conference on Miniturized Systems in Chemistry & Life Sciences, T. Laurell, J. Nilsson, K. Jensen, D.J. Harrison, and J.P. Kutter, eds., Royal Society of Chemistry, Cambridge, UK, vol. 1, no month given, 2004, pp. 348-349.*
Rocklin et al., "A Microfabricated Fluidic Device for Performing Two-Dimensional Liquid-Phase Separations", Analytical Chemistry, vol. 72, No. 21, Nov. 1, 2000, p. 5244-5249.*
Leinweber et al., "Nonequilibrium Electrokinetic Effects in Beds of Ion-Permselective Particles", Langmuir, vol. 20, No. 26, 2004, pp. 11637-11648.*

(Continued)

*Primary Examiner*—Nam X Nguyen
*Assistant Examiner*—J. Christopher Ball
(74) *Attorney, Agent, or Firm*—Pearl Cohen Zedek Latzer, LLP; Mark S. Cohen

(57) ABSTRACT

The present invention provides a device and methods of use thereof in concentrating a species of interest and/or controlling liquid flow in a device. The methods, inter-alia, make use of a device comprising microchannels, which are linked to nanochannels, whereby induction of an electric field in the nanochannel results in ion depletion in the linkage region between the microchannel and nanochannel, and a space charge layer is formed within the microchannel, which provides an energy barrier for said species of interest which enables its concentration in a region in the microchannel.

74 Claims, 8 Drawing Sheets

OTHER PUBLICATIONS

Petersen, N.J. et al., Study of Interface Conductivity and Its Possible Applications, Proceedings 8th International Conference on Miniturized Systems for Chemistry and Life Science, Edited by T. Laurell et al. Cambridge, UK: Royal Society of Chemistry, Sep. 2004, vol. 1, p. 348-349. Entire Doc.

Lefnweber, F.C. et al., Non-equilibrium Electrokinetic Effects in Beds of Ion-Permselective Particles, Langmuir, 2004, vol. 20, pp. 11637-11648. Entire Doc US 6.326,083 BI (Yang et al.) Dec. 4, 2001, col. 23, line 25-27.

* cited by examiner

A

B

ELECTROKINETIC CONCENTRATION DEVICE AND METHODS OF USE THEREOF

CROSS REFERENCE TO RELATED APPLICATIONS

This invention claims the benefit of U.S. Provisional Application Ser. No. 60/646,513, which was filed Jan. 25, 2005, which is hereby incorporated in its entirety.

GOVERNMENT INTEREST STATEMENT

This invention was made in whole or in part with government support under grant number CTS-0347348, awarded by the National Science Foundation and grant number F19628-00-C-0002, awarded by the, United States Air Force. The government may have certain rights in the invention.

FIELD OF THE INVENTION

This invention provides devices and methods of use thereof in concentrating a charged species of interest in solution. This invention provides a concentration device, which is based on electrokinetic trapping of a charged species of interest, which can be further isolated and analyzed.

BACKGROUND OF THE INVENTION

One of the major challenges of proteomics is the sheer complexity of biomolecule samples, such as blood serum or cell extract. Typical blood samples could contain more than 10,000 different protein species, with concentrations varying over 9 orders of magnitude. Such diversity of proteins, as well as their huge concentration ranges, poses a formidable challenge for sample preparation in proteomics.

Conventional protein analysis techniques, based on multidimensional separation steps and mass spectrometry (MS), fall short because of the limited separation peak capacity (up to ~3000) and dynamic range of detection (~$10^4$). Microfluidic biomolecule analysis systems (so-called μTAS) hold promise for automated biomolecule processing. Various biomolecule separation and purification steps, as well as chemical reaction and amplification has been miniaturized on a microchip, demonstrating orders of magnitude faster sample separation and processing. In addition, microfluidic integration of two different separation steps into a multidimensional separation device has been demonstrated. However, most microfluidic separation and sample processing devices suffers from the critical issue of sample volume mismatch. Microfluidic devices are very efficient in handling and processing 1 pL~1 nL of sample fluids, but most biomolecule samples are available or handled in a liquid volume larger than 1 μL. Therefore, microchip-based separation techniques often analyze only a small fraction of available samples, which significantly limits the overall detection sensitivity. In proteomics, this problem is exacerbated by the fact that information-rich signaling molecules (cytokines and biomarkers, e.g.) are present only in trace concentrations (nM~pM range), and there is no signal amplification technique such as polymerase chain reaction (PCR) for proteins and peptides.

What is needed is an efficient sample concentrator, which can take typical sample volume of microliters or more and concentrate molecules into a smaller volume so that it can be separated and detected much more sensitively. Several strategies are currently available to provide sample preconcentration in liquid, including field-amplified sample stacking (FAS), isotachophoresis(ITP), electrokinetic trapping, micellar electrokinetic sweeping, chromatographic preconcentration, and membrane preconcentration. Many of these techniques are originally developed for capillary electrophoresis, and require special buffer arrangements and/or reagents. Efficiency of chromatographic and filtration-based preconcentration techniques depends on the hydrophobicity and the size of the target molecules. Electrokinetic trapping can be used for any charged biomolecule species, but generally requires nanoporous charge-selective membranes for the operation. Overall, the demonstrated concentration factors for the existing preconcentration schemes are limited to ~1000, and their application to the integrated Microsystems is difficult due to various operational constraints such as reagents and materials requirements.

SUMMARY OF THE INVENTION

The invention provides, in one embodiment, a concentrating device comprising:
- a microchannel;
- a nanochannel;
- a unit to induce an electric field in said nanochannel;
- a unit to induce an electrokinetic or pressure driven flow in said microchannel; and
- a conduit, through which a liquid comprising a species of interest can be made to pass;

wherein said microchannel is linked to said nanochannel, and said conduit is linked to said microchannel.

In one embodiment, the introduction of a liquid comprising a species of interest in said device and independent induction of said electric field in said nanochannel and in said microchannel, concentrates said species of interest within said microchannel.

In another embodiment, the means for inducing an electric field in the nanochannel, or in said microchannel, or combination thereof, is a voltage supply. In one embodiment, the voltage applied is between 50 mV and 500 V. In one embodiment, the voltage supply applies equal voltage to the anodic and cathodic side of the microchannel, or in another embodiment, the voltage supply applies greater voltage to the anodic side of said microchannel, as compared to the cathodic side.

In one embodiment, the width of the microchannel is between 1-100 μm, and in another embodiment, the depth of the microchannel is between 0.5-50 μm. In another embodiment, the width of the nanochannel is between 1 μm-50 μm, and in another embodiment, the depth of said nanochannel is between 20-100 nanometers.

In one embodiment, the surface of the microchannel has been functionalized to reduce or enhance adsorption of said species of interest to said surface. In another embodiment, the surface of the nanochannel and/or microchannel has been functionalized to enhance or reduce the operation efficiency of the device. In another embodiment, external gate potential is applied to the substrate of the device, to enhance or reduce the operation efficiency of the device. In another embodiment, the device is comprised of a transparent material. In another embodiment, the transparent material is pyrex, silicon dioxide, silicon nitride, quartz or SU-8.

In another embodiment, the device is coupled to a separation system, or in another embodiment, a detection system, or in another embodiment, an analysis system or in another embodiment, a combination thereof. In another embodiment, the device is coupled to an illumination source.

In another embodiment, the device comprises multiple microchannels, nanochannels or combinations thereof. In one embodiment, the microchannels, nanochannels or combinations thereof are arranged with a particular geometry, which in one embodiment, comprises perpendicular orientation of the microchannels with respect to said nanochannels.

In one embodiment, the invention provides for a method of concentrating a species of interest in a liquid, comprising using a device of the invention.

In one embodiment, this invention provides a microfluidic pump comprising a device of this invention, which in one embodiment has a liquid flow speed of between 10 µm/sec and 10 mm/sec.

In one embodiment, this invention provides a method of concentrating a species of interest in a liquid, the method comprising the steps of:

introducing liquid from a source into a concentrating device, wherein said liquid comprises a species of interest and wherein said device comprises a microchannel linked to a nanochannel;

inducing an electric field in said nanochannel whereby ion depletion occurs in a region wherein said microchannel is linked to said nanochannel, and a space charge layer is formed within said microchannel, which provides an energy barrier to said species of interest; and inducing liquid flow in said microchannel In one embodiment, the flow is electroosmotic, and in another embodiment, the electroosmotic flow is induced in the microchannel via induction of an electric field in the microchannel. In another embodiment, the flow is pressure driven.

In one embodiment, equal voltage is applied to the anodic and cathodic side of the microchannel, or in another embodiment, greater voltage is applied to the anodic side of the microchannel, as compared to the cathodic side. In another embodiment, a space charge layer is generated in the microchannel prior to applying greater voltage to the anodic side of said microchannel.

In one embodiment, the liquid is a solution. In another embodiment the liquid is a suspension, which, in another embodiment is an organ homogenate, cell extract or blood sample. In one embodiment, the species of interest comprises proteins, polypeptides, nucleic acids, viral particles, or combinations thereof.

In one embodiment, the method further comprises the step of subjecting the species of interest to capillary electrophoresis. In one embodiment, the method further comprises the step of releasing the species of interest from the device. In another embodiment, the method is utilized to detect said species of interest when said species is present in said liquid at a concentration, which is below a limit of detection.

In another embodiment, this invention provides a method for controlling liquid flow in a system, the method comprising:

applying said liquid from a source to a pumping device in said system, wherein said device comprises a microchannel linked to a nanochannel and said liquid comprises a charged species or an amphoteric species;

inducing an electric field in said nanochannel whereby ion depletion occurs in a region wherein said microchannel is linked to said nanochannel, and a space charge layer is formed within said microchannel, which provides an energy barrier for said species of interest; and inducing an electric field in said microchannel whereby electroosmotic flow is induced in said microchannel, said flow further introducing said liquid into said device and said flow is controlled by the strength of said electric field.

DETAILED DESCRIPTION OF THE INVENTION

Figure 1:
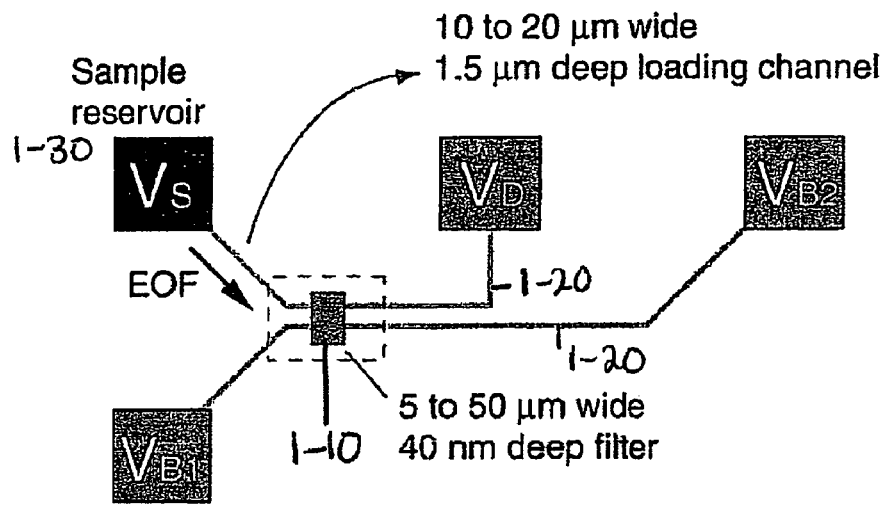
FIG. 1 schematically depicts embodiments of a protein concentration device. (A) An embodiment of the layout of the device. (B) Schematic diagram showing an enlargement of the dotted boxed region in (A). The orientation of the nanochannel (1-10) with respect to the microchannel (1-20) is shown. Applying respective voltages causes the formation of the trapping region (1-40) and depletion region (1-50), as indicated in the drawing, ultimately facilitating electroosmotic flow (EOF) of fluid from the sample reservoir (1-30). $E_T$ specifies the electrical field applied across the ion depletion region, while the $E_n$ specifies the cross nanofilter electrical field.
Figure 1:
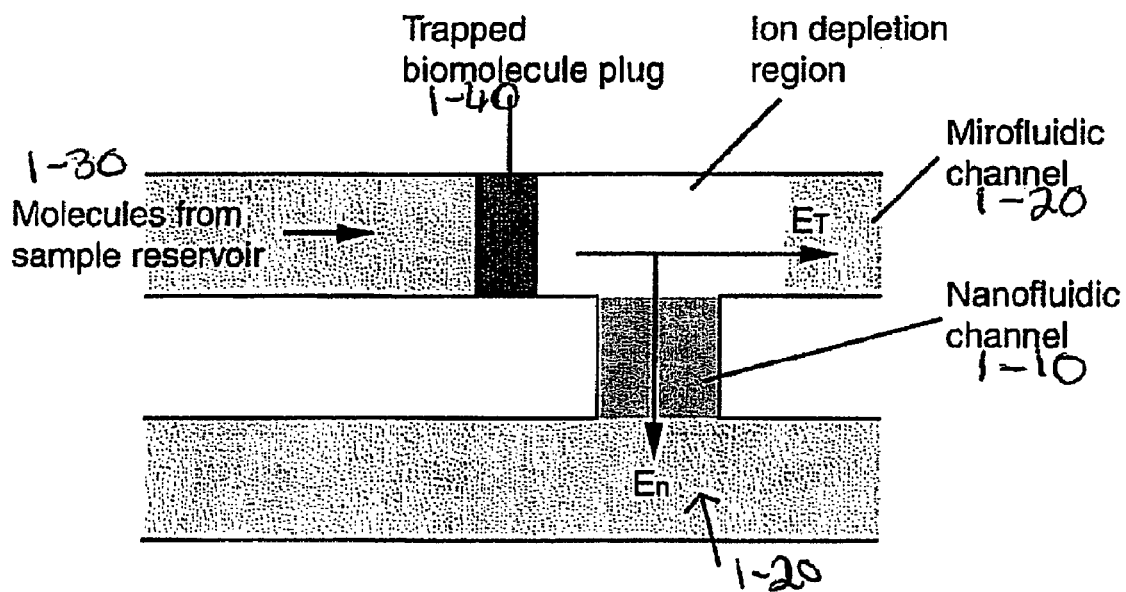

This invention provides, in one embodiment, a concentrating device and methods of use thereof, in concentrating a species of interest.

In one embodiment, the invention provides a concentrating device comprising:
 a microchannel;
 a nanochannel;
 a unit to induce an electric field in said nanochannel;
 a unit to induce an electrokinetic or pressure driven flow in said microchannel; and
 a conduit, through which a liquid comprising a species of interest can be made to pass;
wherein the microchannel is linked to the nanochannel, and the conduit is linked to the microchannel.

The concentrating device, which is referred to as a "concentrator", in another embodiment, comprises at least one microchannel and at least one nanochannel. In one embodiment, the concentrator is formed using the technology of microfabrication and nanofabrication, for formation of the respective channels.

Microfabrication technology, or microtechnology or MEMS, in one embodiment, applies the tools and processes of semiconductor fabrication to the formation of, for example, physical structures. Microfabrication technology allows one, in one embodiment, to precisely design features (e.g., wells, channels) with dimensions in the range of <1 mm to several centimeters on chips made, in other embodiments, of silicon, glass, or plastics. Such technology may be used to construct the microchannels of the concentrator, in one embodiment.

In another embodiment, NEMS or nanotechnology is used to construct the nanochannels of the concentrator. In one embodiment, the nanochannels can be fabricated with nanoimprint lithography (NWL), as described in Z. N. Yu, P. Deshpande, W. Wu, J. Wang and S. Y. Chou, Appl. Phys. Lett. 77 (7), 927 (2000); S. Y. Chou, P. R. Krauss, and P. J. Renstrom, Appl. Phys. Lett. 67 (21), 3114 (1995); Stephen Y. Chou, Peter R. Krauss and Preston J. Renstrom, Science 272, 85 (1996) and U.S. Pat. No. 5,772,905 hereby incorporated herein, in their entirety, by reference. In one embodiment, the nanochannels and/or microchannels can be formed by nanoimprint lithography, interference lithography, self-assembled copolymer pattern transfer, spin coating, electron beam lithography, focused ion beam milling, photolithography, reactive ion-etching, wet-etching, plasma-enhanced chemical vapor deposition, electron beam evaporation, sputter deposition, and combinations thereof. Alternatively, other conventional methods can be used to form the nanochannels and/or microchannels.

In one embodiment, the nanochannels and microchannels are formed as exemplified hereinbelow in Example 1, and as described in J. Han, H. G. Craighead, J. Vac. Sci. Technol., A 17, 2142-2147 (1999) and J. Han, H. G. Craighead, Science 288, 1026-1029 (2000), hereby incorporated fully herein by reference.

In one embodiment, a series of reactive ion etchings are conducted, after which nanochannels are patterned with standard lithography tools. In one embodiment, the etchings are conducted with a particular geometry, which, in another embodiment, determines the interface between the microchannels, and/or nanochannels. In one embodiment, etchings, which create the microchannels, are performed parallel to the plane in which etchings for the nanochannels were created. In another embodiment, additional etching, such as, for example, and in one embodiment, KOH etching was used, to produce additional structures in the concentrator, such as, for example, for creating loading holes.

In another embodiment, electrical insulation of the concentrator is conducted. In one embodiment, such insulation is accomplished via nitride stripping and thermal oxidation of the concentrator. In another embodiment, a surface of the concentrator, which in another embodiment is the bottom surface, may be affixed to a substrate, such as, for example, and in one embodiment, a Pyrex wafer. In one embodiment, the wafer may be affixed using anodic bonding techniques.

In one embodiment, construction of the concentrator may be accomplished by methods known to one skilled in the art, or adaptation of such methods, such as, for example those described in U.S. Pat. No. 6,753,200, fully incorporated herein by reference.

In one embodiment, the fabrication may use a shaped sacrificial layer, which is sandwiched between permanent floor and ceiling layers, with the shape of the sacrificial layer defining a working gap. When the sacrificial layer is removed, the working gap becomes a fluid channel having the desired configuration. This approach, in one embodiment, allows a precise definition of the height, width and shape of interior working spaces, or fluid channels, in the structure of a fluidic device.

The sacrificial layer is formed on a substrate, is shaped by a suitable lithographic process, for example, and is covered by a ceiling layer. Thereafter, the sacrificial layer may be removed with a wet chemical etch, leaving behind empty spaces between the floor and ceiling layers which form working gaps which may be used as flow channels and chambers for the concentrator. In such a device, the vertical dimension, or height, of a working gap is determined by the thickness of the sacrificial layer film, which is made with precise chemical vapor deposition (CVD) techniques, and accordingly, this dimension can be very small.

In order to provide access to the sacrificial layer contained in the structure for the etching solution, which is used to remove the sacrificial layer, one or more access holes may be cut through the ceiling layer, with the wet etch removing the sacrificial layer through these holes. An extremely high etch selectivity may be required between the sacrificial layer and the dielectric layers in order to allow the etch to proceed in the sacrificial layer a significant distance laterally from the access holes without consuming the floor and ceiling layers which compose the finished device. One combination of materials, which may be used for such a process is polysilicon and silicon nitride, for the sacrificial layer and for the floor and ceiling layers, respectively. Extremely high etch selectivities can be obtained with basic solutions such as, in some embodiments, potassium hydroxide (KOH), sodium hydroxide (NaOH), or in another embodiment, tetramethyl ammonium hydroxide (TMAH).

The access holes cut in the top layer may be covered, in another embodiment. For this purpose, a sealing layer of silicon dioxide may be deposited on top of the ceiling lay to fill in the access holes, and this additional thin film layer provides a good seal against leakage or evaporation of fluids in the working gap. SiO2 CVD techniques, represent other embodiments, which yield a low degree of film conformality, such as very low temperature oxide (VLTO) deposition, form a reliable seal without excessive loss of device area due to clogging near the access holes. If desired, the access holes may be drilled through the bottom layer, instead of or in addition to the holes in the ceiling layer, and later resealed by depositing a layer of silicon dioxide.

For example, in some embodiments, chemical vapor deposition (CVD) may be used to deposit the device materials, including permanent wall materials, which are usually a dielectric material such as silicon nitride or silicon dioxide, and nonpermanent sacrificial layer materials, such as amorphous silicon or polysilicon.

In one embodiment, the microchannel and nanochannel are oriented perpendicularly, with respect to each other. In one embodiment, the term "perpendicular" or "perpendicularly" refers to an orientation of one channel being at a 90° angle with respect to the longitudinal axis of another channel, ±5 or in another embodiment, at a 90° angle of ±10°, or in another embodiment, at a 90° angle ±20°.

In one embodiment, an interface region is constructed which connects the microchannel and nanochannel of the concentrator of this invention. In one embodiment, diffraction gradient lithography (DGL) is used to form a gradient interface between the microchannels and nanochannels of this invention. In one embodiment, the gradient interface region may regulate flow through the concentrator, or in another embodiment, regulate the space charge layer formed in the microchannel, which, in another embodiment, may be reflected in the strength of electric field, or in another embodiment, the voltage needed to generate the space charge layer in the microchannel.

In one embodiment, the gradient interface area is formed of lateral spatial gradient structures for narrowing the cross section of a value from the micron to the nanometer length scale. In another embodiment, the gradient interface area is formed of a vertical sloped gradient structure. In another embodiment, the gradient structure can provide both a lateral and vertical gradient.

In one embodiment, the concentrating device may be fabricated by diffraction gradient lithography, by forming a nanochannel or nanochannels on a substrate, forming a microchannel or microchannels on the substrate and forming a gradient interface area between them. The gradient interface area can be formed, in one embodiment, by using a blocking mask positioned above a photo mask and/or photoresist during photolithography. The edge of the blocking mask provides diffraction to cast a gradient light intensity on the photoresist.

In one embodiment, a concentrator may comprise a plurality of channels, including a plurality of microchannels, or a plurality of nanochannels, or a combination thereof. In one embodiment, the phrase "a plurality of channels refers to more than two channels, or, in another embodiment, more than 5, or, in other embodiments, more than 10, 96, 100, 384, 1,000, 1,536, 10,000, 100,000 or 1,000,000 channels.

In one embodiment, the width of the microchannel is between 1-100 μm, or in another embodiment, between 1 and 15 μm, or in another embodiment, between 20 and 50 μm, or in another embodiment, between 25 and 75 μm, or in another embodiment, between 50 and 100 μm. In one embodiment, the depth of the microchannel is between 0.5-50 μmμm, or in another embodiment, between 0.5 and 5 μm, or in another embodiment, between 5 and 15 μm, or in another embodiment, between 10 and 25 μm, or in another embodiment, between 15 and 50 μm.

In another embodiment, the width of the nanochannel is between 1 μm-50 μm, or in another embodiment, between 1 and 15 μm, or in another embodiment, between 10 and 25 μm, or in another embodiment, between 15 and 40 μm, or in another embodiment, between 25 and 50 μm. In another embodiment, the depth of said nanochannel is between 20-100 nanometers, or in another embodiment, between 20 and 50 nanometers, or in another embodiment, between 20 and 75 nanometers, or in another embodiment, between 30 and 75 nanometers or in another embodiment, between 50 and 100 nanometers.

In one embodiment, the concentrator is constructed as diagrammed in FIG. 1. The nanochannel (1-10), which is 5-50 μm wide and 40 nm deep is oriented perpendicularly to the microchannel (1-10), where the microchannel is between 10-20 μm wide and 1.5 μm deep.

In another aspect of the invention, the concentrator further comprises at least one sample reservoir in fluid communication with the microchannel or microchannels. In the embodiment depicted in FIG. 1, the sample reservoir is proximal to the microchannel (1-30). In another embodiment, the sample reservoir is capable of releasing a fluid or liquid comprising a species of interest. In one embodiment, the sample reservoir is connected to the microchannel by means of a conduit, which may have the dimensions of the microchannel, or may comprise a gradient interface area, as described.

In one embodiment, the introduction of a liquid comprising a species of interest in the device and independent induction of an electric field in the nanochannel and in the microchannel, concentrates the species of interest within the microchannel.

In one embodiment, the concentrator makes use of flat nanofluidic filters filled with buffer solution as an ion-selective membrane to generate ion-depletion regions for electrokinetic trapping, as exemplified hereinbelow.

In one embodiment, the device collects charged molecules efficiently because of a nonlinear electroosmotic flow (much stronger than normal electroosmotic flow) generated in the microchannel, which draws fluid into the microchannels from the sample resevoir with high flow speed, and because an energy barrier for anionic molecules is generated by the induced space charge layer in the microchannel, at regions of apposition to the nanochannels.

In one embodiment, two separate electric fields are applied to the concentrator and controlled independently, as shown in FIG. 1B. The field in the nanofluidic channel (En) generates an ion-depletion region and extended space charge layer that traps the anionic molecules. The tangential field in the microfluidic channel (ET), in the anodic side, generates electroosmotic flow, which draws molecules into the. trapped region (1-40) from the reservoir.

Figure 7:
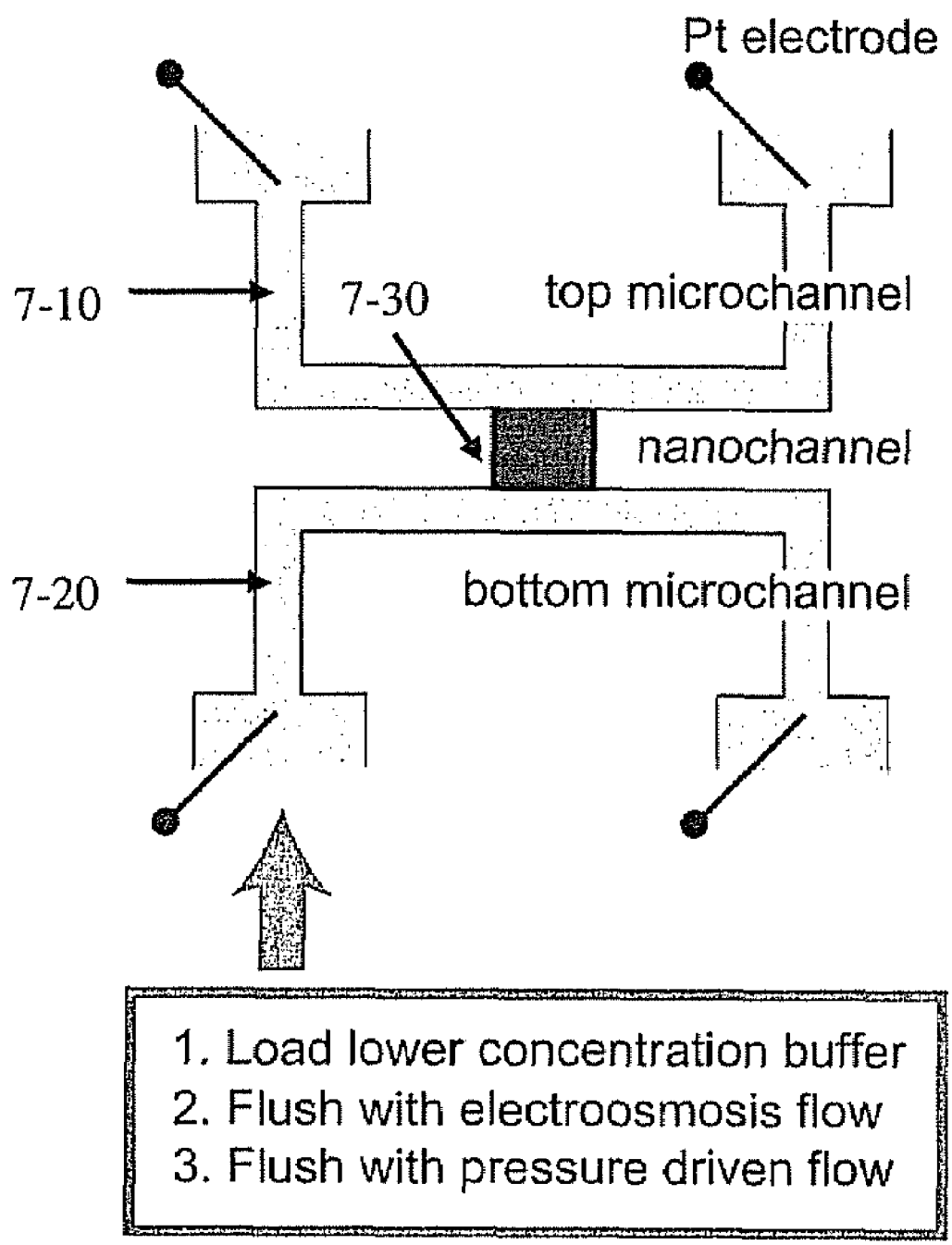
FIG. 7 depicts an embodiment of a device of this invention, wherein different buffer concentrations are used for concentration of a species of interest.

In one embodiment, the space charge region is further stabilized by manipulating buffer conditions in the devices of the invention, for example, as depicted in FIG. 7, and as described further hereinbelow. In one embodiment, the device comprises two or a series of two microchannels, each connected by a nanochannel. According to this embodiment, over a course of time, ion depletion in the top microchannel leads to ion enrichment in the bottom microchannel, thus the buffer concentration in the bottom microfluidic channel increases with prolonged conduction of the separation process. By providing a lower concentration buffer, at prescribed time periods, in one embodiment, or continually, in another embodiment, by electroosmosis, or in another embodiment, by pressure driven flow, in the lower microchannel, this effect is mitigated, according to this embodiment.

Figure 8:
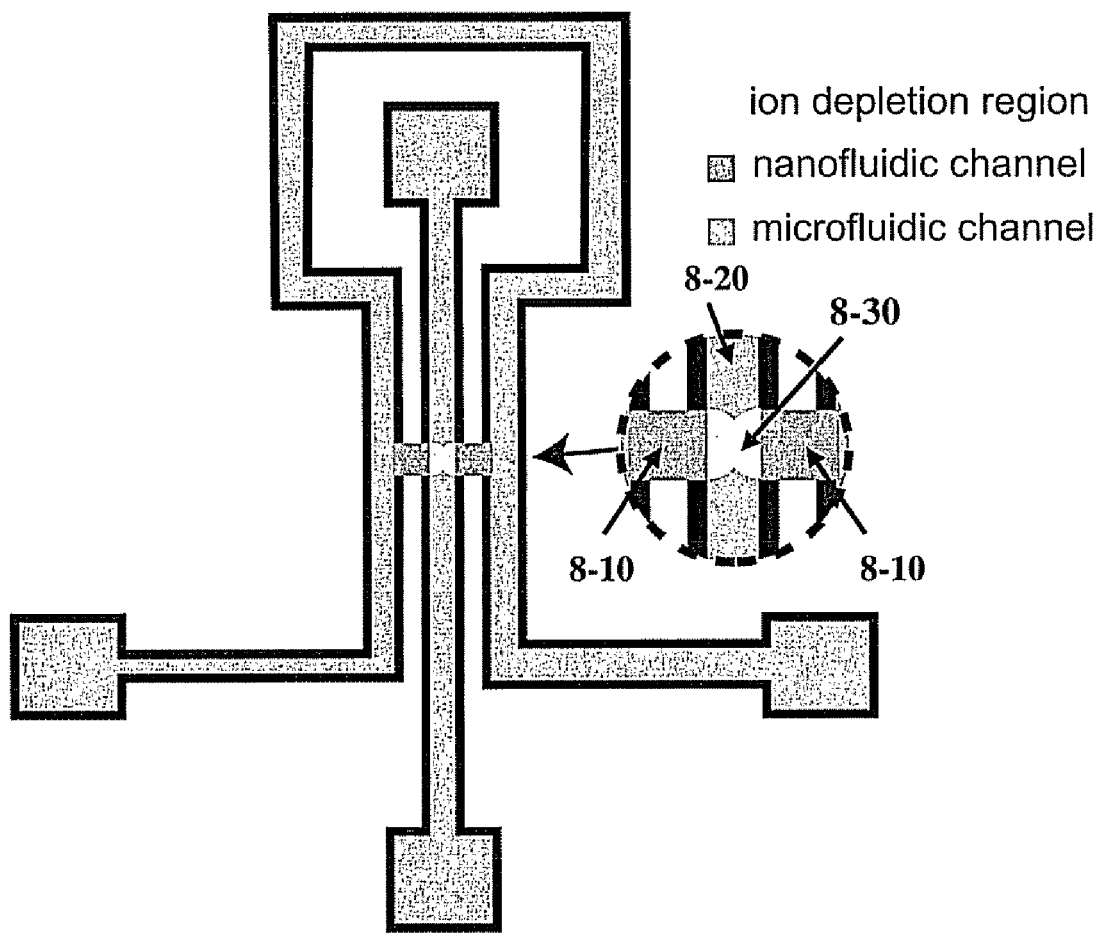
FIG. 8 depicts an embodiment of a device of this invention, wherein each microchannel comprising the sample to be concentrated is connected to two nanochannels oriented perpendicularly thereto.

In another embodiment of the invention, preconcentration of the material may be enhanced by positioning nanofluidic channels on both sides of the microchannel and in fluid communication with the microchannel as shown, for example, in FIG. 8. Ion depletion initiation at the interface between the microchannel and the nanochannel, is enhanced by positioning the nanochannels on either side of the microchannel, and in some embodiments, a more stable space charge region is produced.

In one embodiment, the flow may be pressure-driven, and may be accomplished by any means well known to one skilled in the art. In another embodiment, the flow may be a hybrid of pressure-driven and electrokinetic flow.

In one embodiment, the phrases "pressure-driven flow" refers to flow that is driven by a pressure source external to the channel segment through which such flow is driven, as contrasted to flow that is generated through the channel segment in question by the application of an electric field through that channel segment, which is referred to herein, in one embodiment, as "electrokinetically driven flow."

Examples of pressure sources include negative and positive pressure sources or pumps external to the channel segment in question, including electrokinetic pressure pumps, e.g., pumps that generate pressure by electrokinetically driven flow in a pumping channel that is separate from the channel segment in question, provided such pumps are external to the channel segment in question (see, U.S. Pat. Nos. 6,012,902 and 6,171,067, each of which is incorporated herein by reference in its entirety for all purposes).

In one embodiment, the term "electrokinetic flow" refers to the movement of fluid or fluid borne material under an applied electric field. Electrokinetic flow generally encompasses one or both of electrophoresis, e.g., the movement of charged species through the medium or fluid in which it is disposed, as well as electroosmosis, e.g., the electrically driven movement of the bulk fluid, including all of its components. Accordingly, when referred to in terms of electrokinetic flow, it will be appreciated that what is envisioned is the full spectrum of electrokinetic flow from predominantly or substantially completely electrophoretic movement of species, to predominantly electroosmotically driven movement of material, e.g., in the case of uncharged material, and all of the ranges and ratios of the two types of electrokinetic movement that fall between these extremes.

In one embodiment, reference to the term "liquid flow" may encompass any or all of the characteristics of flow of fluid or other material through a passage, conduit, channel or across a surface. Such characteristics include without limitation the flow rate, flow volume, the conformation and accompanying dispersion profile of the flowing fluid or other material, as well as other more generalized characteristics of flow, e.g., laminar flow, creeping flow, turbulent flow, etc.

In one embodiment, hybrid flow may comprise pressure-based relay of the liquid sample into the channel network, followed by electrokinetic movement of materials, or in another embodiment, electrokinetic movement of the liquid followed by pressure-driven flow.

In one embodiment, the electric field may be induced in the respective channels by applying voltage from a voltage supply to the device. In one embodiment voltage is applied by way of the placement of at least one pair of electrodes capable of applying an electric field across at least some of the channels in at least one direction. Electrode metal contacts can be integrated using standard integrated circuit fabrication technology to be in contact with at least one microchannel, or in another embodiment, at least one nanochannel, or in another embodiment, a combination thereof, and oriented as such, to establish a directional electric field. Alternating current (AC), direct current (DC), or both types of fields can be applied. The electrodes can be made of almost any metal, and in one embodiment, comprise thin Al/Au metal layers deposited on defined line paths. In one embodiment, at least one end of one electrode is in contact with buffer solution in the reservoir.

In another embodiment, the concentrator may contain at least two pairs of electrodes, each providing an electric field in different directions. In one embodiment, field contacts can be used to independently modulate the direction and amplitudes of the electric fields to, in one embodiment, orient the space charge layer, or in another embodiment, move macromolecules at desired speed or direction, or in another embodiment, a combination thereof.

In one embodiment, the voltage applied is between 50 mV and 500 V. In one embodiment, the voltage supply applies equal voltage to the anodic and cathodic side of the microchannel, or in another embodiment, the voltage supply applies greater voltage to the anodic side of said microchannel, as compared to the cathodic side.

In one embodiment, the voltage supply may be any electrical source, which may be used to provide the desired voltage. The electrical source may be any source of electricity capable of generating the desired voltage. For example, the electrical source may be a pizoelectrical source, a battery, or a device powered by household current. In one embodiment, a pizoelectrical discharge from a gas igniter may be used.

In one embodiment, the electrokinetic trapping in the device and sample collection can occur over a course of minutes, or in another embodiment, can be maintained for several hours. In one embodiment, concentration over a course of time results in concentration factors as high as $10^6$-$10^8$, and in another embodiment, may be even higher, upon optimization of the conditions employed during the concentration, such as by modifying the interface between the microchannel and nanochannel, voltage applied, salt concentration of the liquid, pH of the liquid, or combination thereof.

In another embodiment, the concentrator further comprises at least one waste reservoir in fluid communication with the microchannel, microchannels, nanochannel or nanochannels of the concentrator. In one embodiment, the waste reservoir is capable of receiving a fluid.

In one embodiment, the surface of the microchannel may be functionalized to reduce or enhance adsorption of the species of interest to the surface of the concentrator. In another embodiment, the surface of the nanochannel and/or microchannel has been functionalized to enhance or reduce the operation efficiency of the device. In another embodiment, external gate potential is applied to the substrate of the device, to enhance or reduce the operation efficiency of the device. In another embodiment, the device is comprised of a transparent material. In another embodiment, the transparent material is pyrex, silicon dioxide, silicon nitride, quartz or SU-8.

In another embodiment, the concentrator is adapted such that analysis of a species of interest may be conducted, in one embodiment, in the concentrator, or in another embodiment, downstream of the concentrator. In one embodiment, analysis downstream of the concentrator refers to removal of the concentrated species from the device, and placement in an appropriate setting for analysis, or in another embodiment, construction of a conduit from the concentrator which relays the concentrated material to an appropriate setting for analysis. In one embodiment, such analysis may comprise signal acquisition, and in another embodiment, a data processor. In one embodiment, the signal can be a photon, electrical current/impedance measurement or change in measurements. It is to be understood that the concentrating device of this invention may be useful in various analytical systems, including bioanalysis Microsystems, due to its simplicity, performance, robustness, and integrabilty to other separation and detection systems, and any integration of the device into such a system is to be considered as part of this invention.

In another embodiment, the concentrator, or in another embodiment, the microchannel or microchannels are capable of being imaged with a two-dimensional detector. Imaging of the concentrator, or parts thereof, may be accomplished by presenting it to a suitable apparatus for the collection of emitted signals, such as, in some embodiments, optical elements for the collection of light from the microchannels.

In another embodiment, the device is coupled to a separation system, or in another embodiment, a detection system, or in another embodiment, an analysis system or in another embodiment, a combination thereof. In another embodiment, the device is coupled to an illumination source.

In one embodiment, the concentrator may be disposable, and in another embodiment, may be individually packaged, and in another embodiment, have a sample loading capacity of 1-50,000 individual fluid samples. In one embodiment, the concentrator can be encased in a suitable housing, such as plastic, to provide a convenient and commercially-ready cartridge or cassette. In one embodiment, the concentrator will have suitable features on or in the housing for inserting, guiding, and aligning the device, such that, for example, a sample loading compartment is aligned with a reservoir in another device, which is to be coupled to the concentrator. For example, the concentrator may be equipped with insertion slots, tracks, or a combination thereof, or other adaptations for automation of the concentration process via a device of this invention.

The concentrator may be so adapted, in one embodiment, for high throughput screening of multiple samples, such as will be useful in proteomics applications, as will be appreciated by one skilled in the art.

In one embodiment, the concentrator is connected to electrodes, which are connected to an electric potential generator, which may, in another embodiment be connected with metal contacts. Suitable metal contacts can be external contact patches that can be connected to an external scanning/imaging/electric-field tuner, in another embodiment.

In one embodiment of the present invention, the concentrator is a part of a larger system, which includes an apparatus to excite molecules inside the channels and detect and collect the resulting signals. In one embodiment, a laser beam may be focused upon the sample plug, using a focusing lens, in another embodiment. The generated light signal from the molecules inside the microchannels may be collected by focusing/collection lens, and, in another embodiment, reflected off a dichroic mirror/band pass filter into optical path, which may, in another embodiment, be fed into a CCD (charge coupled device) camera.

In another embodiment, an exciting light source could be passed through a dichroic mirror/band pass filter box and focusing/collecting scheme from the top of the concentrator.

Various optical components and devices can also be used in the system to detect optical signals, such as digital cameras, PMTs (photomultiplier tubes), and APDs (Avalanche photodiodes).

In another embodiment, the system may further include a data processor. In one embodiment, the data processor can be used to process the signals from a CCD, to a digital image of the concentrated species onto a display. In one embodiment, the data processor can also analyze the digital image to provide characterization information, such as size statistics, histograms, karyotypes, mapping, diagnostics information and display the information in suitable form for data readout.

In one embodiment, the device is further modified to contain an active agent in the microchannel. For example, and in one embodiment, the microchannel is coated with an enzyme at a region wherein the concentrated molecules will be trapped, according to the methods of this invention. According to this aspect, the enzyme, such as, a protease, may come into contact with concentrated proteins, and digest them. According to this aspect, the invention provides a method for proteome analysis, wherein, for example, a sample comprising a plurality of cellular polypeptides is concentrated in the microchannel, to obtain a plurality of substantially purified polypeptides. The polypeptide is exposed to a protease immobilized within the microchannel, under conditions sufficient to substantially digest the polypeptide, thereby producing digestion products or peptides. The digestion products may, in another embodiment, then be transported to a downstream separation module where they are separated, and in another embodiment, from there, the separated digestion products may be conveyed to a peptide analysis module. The amino acid sequences of the digestion products may be determined and assembled to generate a sequence of the polypeptide. Prior to delivery to a peptide analysis module, the peptide may be conveyed to an interfacing module, which in turn, may perform one or more additional steps of separating, concentrating, and or focusing.

In other embodiments, the proteases include, but are not limited to: peptidases, such as aminopeptidases, carboxypeptidases, and endopeptidases (e.g., trypsin, chymotrypsin, thermolysin, endoproteinase Lys C, endoproteinase GluC, endoproteinase ArgC, endoproteinase AspN). Aminopeptidases and carboxypeptidases are useful in characterizing post-translational modifications and processing events. Combinations of proteases also can be used. In one embodiment, the proteases and/or other enzymes can be immobilized onto the microchannel surface using adsorptive or covalent methods. In some embodiments, examples of covalent immobilization include direct covalent attachment of the protease to a surface with ligands such as glutaraldehyde, isothiocyanate, and cyanogen bromide. In other embodiments, the proteases may be attached using binding partners which specifically react with the proteases or which bind to or react with molecules which are themselves coupled to the proteases (e.g., covalently). Binding pairs may include the following: cytostatin/papain, valphosphanate/carboxypeptidase A, biotin/streptavidin, riboflavin/riboflavin binding protein, antigen/antibody binding pairs, or combinations thereof.

In one embodiment, the steps of concentrating polypeptides obtained from a given cell, producing digestion products, and analyzing digestion products to determine protein sequence, can be performed in parallel and/or iteratively for a given sample, providing a proteome map of the cell from which the polypeptides were obtained. Proteome maps from multiple different cells can be compared to identify differentially expressed polypeptides in these cells, and in other embodiments, the cells may be subjected to various treatments, conditions, or extracted from various sources, with the proteome map thus generated reflecting differential protein expression as a result of the status of the cell.

In certain embodiments of the present invention, the concentrator may contain an apparatus for transporting concentrates from the microchannels into the waste reservoirs.

In one embodiment, this invention provides an array architecture that is capable of being scaled to at least 10,000 concentrators, suitable for a real-world screen.

In one embodiment, concentration efficiency may be determined by using labeled proteins or polypeptides, introduced into the concentrator in known ratios and detecting the concentrated labeled protein or polypeptides, such as exemplified hereinbelow. Signal intensity can be determined as a function of time, over background noise.

In one embodiment, the concentrators of this invention may be under controlled physicochemical parameters, which may comprise temperature, pH, salt concentration, or a combination thereof.

In one embodiment, the nanochannel may be replaced by a charged gel or random nanoporous material, wherein charged group are embedded in the nanoporous material. In one embodiment, according to this aspect of the invention, the charged gel or nanoporous material may have a similar pore size. According to this aspect of the invention, a space charge layer may be generated in the charged gel or random nanoporous material, similar to that formed in the nanochannel as described and exemplified herein, wherein an electric field is induced in the nanoporous charged gel or charged material, similar to that induced in the nanochannel.

In one embodiment, the invention provides for a method of concentrating a species of interest in a liquid, comprising using a device of the invention.

In one embodiment, this invention provides a microfluidic pump comprising a device of this invention, which in one embodiment has a liquid flow speed of between 10 µm/sec and 10 mm/sec.

In one embodiment, this invention provides a method of concentrating a species of interest in a liquid, the method comprising the steps of:
  introducing liquid from a source into a concentrating device, wherein said liquid comprises a species of interest and wherein said device comprises a microchannel linked to a nanochannel;
  inducing an electric field in said nanochannel whereby ion depletion occurs in a region wherein said microchannel is linked to said nanochannel, and a space charge layer is formed within said microchannel, which provides an energy barrier to said species of interest; and
  inducing liquid flow in said microchannel In one embodiment, the flow is electroosmotic, and in another embodiment, the electroosmotic flow is induced in the microchannel via induction of an electric field in the microchannel. In another embodiment, the flow is pressure driven.

Figure 2:
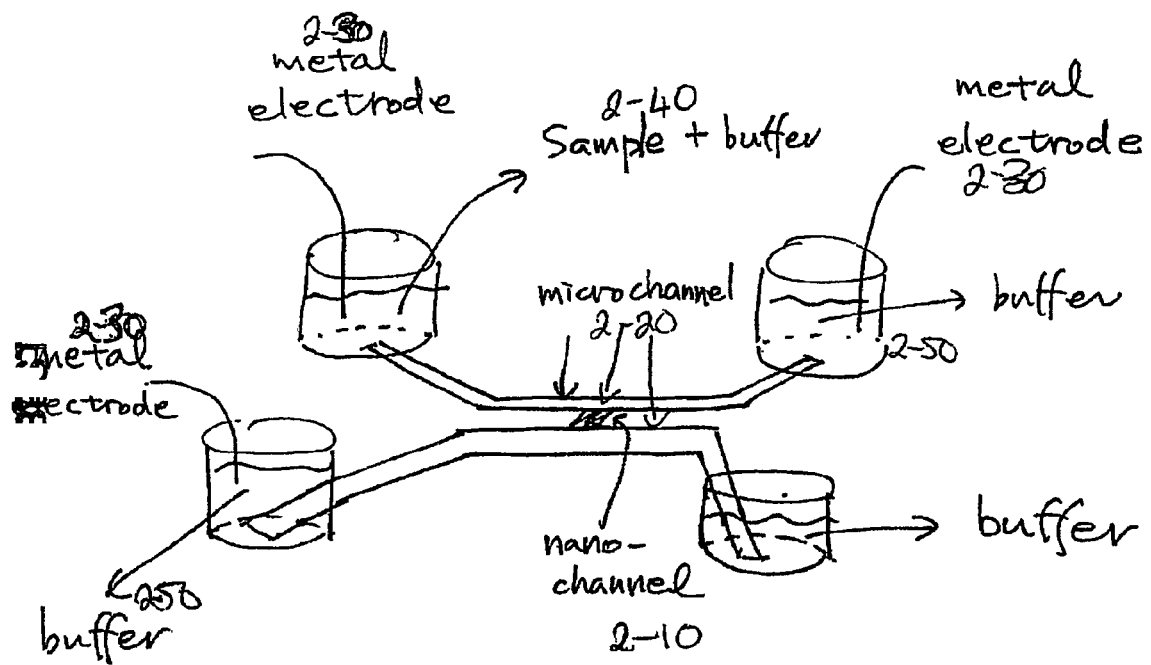
FIG. 2 schematically depicts an embodiment of the protein concentration device. A nanofluidic channel (2-10), connects two microfluidic channels (2-20). Electric fields are applied to the device, by means of the electrodes (2-30), as shown. Molecules are conveyed into the device from the sample reservoir (2-40), as described. Other containers with buffer in contact with the microchannels (2-50), are as indicated.

In one embodiment, within the thin nanofluidic channel, perm-selective portion of ion currents, caused by the counterions within the Debye layer cannot be ignored, compared with the total ion current through the nanochannel, therefore, more counterions (from the Debye layer) than co-ions migrate across the nanochannel when an electric field is applied resulting in a net transfer of charges (counterions) from the anodic side to the cathodic side, and a concentration polarization effect (FIG. 2). According to this aspect of the invention, ion depletion near the nanofluidic channel thickens the Debye layer, causing its overlap more significantly in the nanofluidic channel, speeding up the concentration polarization effect, and above a certain threshold En value, as described further hereinbelow, results in electroosmosis with second order kinetics.

According to this aspect of the invention, counterion depletion from the nanofluidic channel, and creation of an extended space charge layer in bulk solution within the microchannel prevents co-ion migration in this region. In one embodiment, controlling the electric fields (En and ET), to balance the two forces (anion repulsion from the space charge layer vs. nonlinear electroosmotic flow from the reservoir), stabilizes the interface, which is where anionic species of interest are trapped and collected, according to this aspect of the invention.

In one embodiment, equal voltage is applied to the anodic and cathodic side of the microchannel, or in another embodiment, greater voltage is applied to the anodic side of the microchannel, as compared to the cathodic side. In another embodiment, a space charge layer is generated in the microchannel prior to applying greater voltage to the anodic side of said microchannel.

In one embodiment, the liquid is a solution. In another embodiment, the liquid is a suspension, which, in another embodiment is an organ homogenate, cell extract or blood sample. In one embodiment, the species of interest comprises proteins, polypeptides, nucleic acids, viral particles, or combinations thereof. In one embodiment, the species of interest is a protein, nucleic acid, virus or viral particle found in, or secreted from a cell, and in another embodiment, is found in very low quantities, such that it represents less than 10% of the protein extracted form a protein extract of the cell.

In one embodiment, the methods of this invention and the devices of this invention enable collection of molecules from a relatively large (~1 µL or larger) sample volume, and their concentration into a small (1pL~1nL) volume. Such concentrated sample can then, in other embodiments, be efficiently sorted, separated or detected by various microfluidic systems, without sacrificing the overall detection sensitivity caused by the small sample volume capacity of microfluidic biomolecule sorting/detection systems.

In one embodiment, the methods and concentrating devices of this invention allow for significantly increased signal intensity of a molecules, and subsequent just detection, which, in another embodiment, allows for more aggressive molecular sorting and/or removal of high-abundance molecules, such as proteins, from a sample, without sacrificing the detectability of molecules in minute concentration, such as minor proteins or peptides.

In another embodiment, the devices for and methods of concentration of this invention enable the use of several non-labeling detection techniques (UV absorption, for example), which was not possible due to the short path length and small internal volume of conventional microfluidic channels. Therefore, in another embodiment, the devices for and methods of concentration of this invention, which combine concentration and molecular sorting may provide an ideal platform for integrated Microsystems for biomarker detection, environmental analysis, and chemical-biological agent detection.

In one embodiment, the method further comprises the step of releasing the species of interest from the device. In one embodiment, the method further comprises the step of subjecting the species of interest to capillary electrophoresis.

Capillary electrophoresis is a technique that utilizes the electrophoretic nature of molecules and/or the electroosmotic flow of samples in small capillary tubes to separate sample components. Typically a fused silica capillary of 100 µm inner diameter or less is filled with a buffer solution containing an electrolyte. Each end of the capillary is placed in a separate fluidic reservoir containing a buffer electrolyte. A potential voltage is placed in one of the buffer reservoirs and a second potential voltage is placed in the other buffer reservoir. Positively and negatively charged species will migrate in opposite directions through the capillary under the influence of the electric field established by the two potential voltages applied to the buffer reservoirs. The electroosmotic flow and the electrophoretic mobility of each component of a fluid will determine the overall migration for each fluidic component. The fluid flow profile resulting from electroosmotic flow is flat due to the reduction in frictional drag along the walls of the separation channel. The observed mobility is the sum of the electroosmotic and electrophoretic mobilities, and the observed velocity is the sum of the electroosmotic and electrophoretic velocities.

In one embodiment of the invention, a capillary electrophoresis system is micromachined onto a device, which is a part of, or separate from, the concentrating device described herein. Methods of micromachining capillary electrophoresis systems onto devices are well known in the art and are described, for example in U.S. Pat. No. 6,274,089; U.S. Pat. No. 6,271,021; Effenhauser et al., 1993, Anal. Chem. 65: 2637-2642; Harrison et al., 1993, Science 261: 895-897; Jacobson et al., 1994, Anal. Chem. 66:1107-1113; and Jacobson et al., 1994, Anal. Chem. 66: 1114-1118.

In one embodiment, the capillary electrophoresis separations provide a sample which may then be used for both MALDI-MS and/or ESI-MS/MS-based protein analyses (see, e.g., Feng et al., 2000, Journal of the American Society For Mass Spectrometry 11: 94-99; Koziel, New Orleans, La. 2000; Khandurina et al., 1999, Analytical Chemistry 71: 1815-1819.

In other embodiments, downstream separation devices, which may interface with the concentrator of this invention include, but are not limited to, micro high performance liquid chromatographic columns, for example, reverse-phase, ion-exchange, and affinity columns.

It is to be understood that the exact configuration of any systems, devices, etc. which are coupled downstream of the concentrating device are to be considered as part of this invention, and that the configuration may be varied, to suit a desired application. In one embodiment, a module for separation of the concentrated peptides which is positioned downstream of the concentrating device comprises a separation medium and a capillary between the ends of which an electric field is applied. The transport of a separation medium in the capillary system and the injection of the sample to be tested (e.g., a sample band comprising peptides and/or partially digested polypeptides) into the separation medium can be carried out with the aid of pumps and valves, or in another embodiment, via electric fields applied to various points of the capillary.

In another embodiment, the method is utilized to detect said species of interest when said species is present in said liquid at a concentration, which is below a limit of detection.

Figure 3:
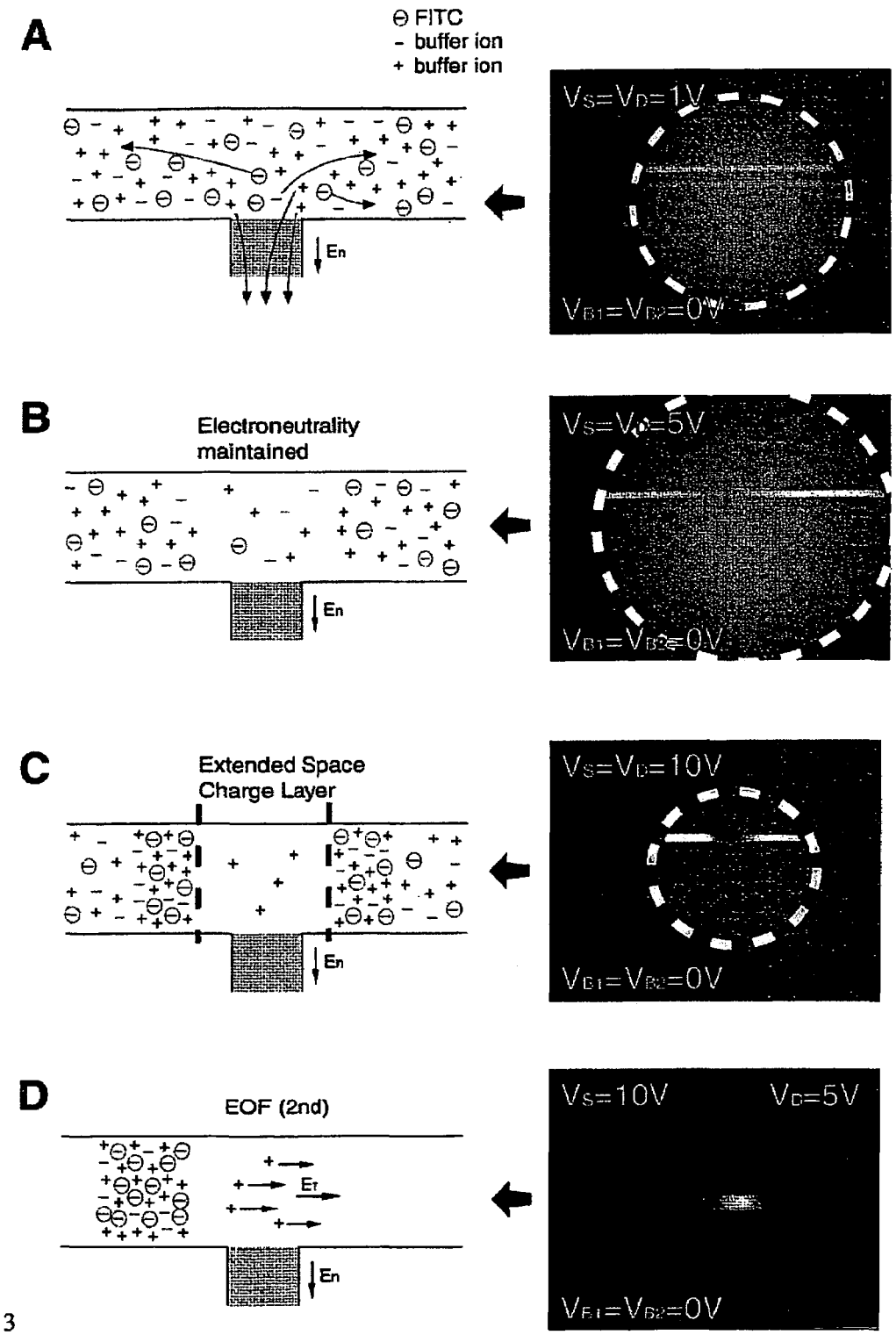
FIG. 3 schematically depicts an embodiment of the mechanism of concentration of the charged species in the device. (A) No concentration polarization effect is observed when a small electrical field is applied across the nanofilter ($E_n$). (B) As the $E_n$ increases, the transport of ions becomes diffusion-limited and generates the ion-depletion zone. However, the region maintains electroneutrality. (C) Once a strong field ($E_n$) is applied, the nanochannel will develop an induced space charge layer, where electroneutrality is no longer maintained. (D) By applying an additional field ($E_T$) along the microfluidic channel in the anodic side (from $V_S$ to $V_D$), a nonlinear electrokinetic flow (called electroosmosis of the second kind) is induced, which results in fast accumulation of biomolecules in front of the induced space charge layer.

As exemplified hereinbelow (FIG. 3), a solution of 33 pM green fluorescent protein (GFP) loaded into the device, when monitored by fluorescence microscopy, was below the limit of detection. Concentration of the solution as described enabled detection of the 33 pM GFP, and that of even more dilute GFP protein solutions of 33 fM, when monitored over approximately 3 hours, with concentration of factors of $10^6$–$10^8$ achieved.

In one embodiment, concentration speed is rapid. As exemplified hereinbelow, $10^7$-fold concentration of the GFP solution was achieved within an hour. Since the approximate volume of concentrated plug is about 0.5 pL (~1.5 μm×20 μm×20 μm), then the concentrating device pumped sample liquid volume as large as 1 μL through the channel and trapped the GFP within that volume. Given the concentration time of ~$10^4$ sec in this experiment, the average sample flow speed should be as high as 1 mm/sec.

In another embodiment, this invention provides a method for controlling liquid flow in a system, the method comprising:

applying said liquid from a source to a pumping device in said system, wherein said device comprises a microchannel linked to a nanochannel and said liquid comprises a charged species or an amphoteric species;

inducing an electric field in said nanochannel whereby ion depletion occurs in a region wherein said microchannel is linked to said nanochannel, and a space charge layer is formed within said microchannel, which provides an energy barrier for said species of interest; and inducing an electric field in said microchannel whereby electroosmotic flow is induced in said microchannel, said flow further introducing said liquid into said device and said flow is controlled by the strength of said electric field.

Controlling liquid flow has numerous application in a wide range of fields, as will be appreciated by one skilled in the art. In one embodiment, the methods of controlling liquid flow, and/or the methods of concentrating a species of interest may be useful in biosensor devices. In one embodiment, control of liquid flow is essential in biosensors, wherein flow and mixing of a sample and various reactants to and from reservoirs in a microfluidic system is required. In another embodiment, concentration of a minute quantity of a species of interest for detection is a critical element of a biosensor device. In one embodiment, such methods are particularly useful in detecting organisms in a latent or spore state, wherein detection of the organism is otherwise difficult.

In other embodiments, various applications of the methods of the present invention are possible without deviating from the present invention. For the method of controlling fluid flow, for example, multiple microchannels may be so deposited such that fluid flow is directed to a central reservoir, to which additional microchannels may be connected. According to this aspect, the fluid once within the reservoir may then be mixed, and in turn, be pumped through the second set of microchannels to another reservoir connected thereto, for further manipulation. It can be appreciated that the pumping method of the present invention works with various types of fluids including water and biological fluids.

By way of example, the concentrating and pumping methods of the present invention allow for high-throughput robotic assaying systems to directly interface with the devices of the present invention, and to concentrate a species of interest, and/or and pump liquid.

Various modes of carrying out the invention are contemplated as being within the scope of the following claims particularly pointing out and distinctly claiming the subject matter, which is regarded as the invention.

EXAMPLES

Materials and Methods

Device Fabrication:

Fabrication techniques were as described (J. Han, H. G. Craighead, *J. Vac. Sci. Technol., A* 17, 2142-2147 (1999); J. Han, H. G. Craighead, *Science* 288, 1026-1029 (2000)). Two reactive ion etchings were used. After patterning the 5-20 µM wide nanochannels with standard lithography tools, the fist reactive ion etching (RIE) etching was conducted for about 10 sec to etch 40 nm nanochannel, while the second etching created two parallel 1.5 µm microfluidic channels across the nanofilter. Nanofilters with a depth between 30 and 70 nm were fabricated to demonstrate the effects of buffer concentration and channel depth. After completing RIE etching, KOH etching was used to etch through the loading holes. Thermal oxidation was conducted following nitride stripping, which provided proper electrical insulation. The bottom of the device was then bonded with a Pyrex wafer using standard anodic bonding techniques.

Biomolecule and Reagent Preparation

A 10 mM phosphate buffer (dibasic sodium phosphate) at pH 9.1 was mainly used, supplemented with 10 µM EDTA to prevent bacterial growth. Successful pre-concentration was demonstrated under conditions of pH 4.6, 10 mM phosphate buffer, as well. Conditions of 10 mM pH 3.5 acetate buffer, and 1×TBE buffer (~80 mM) were without significant pre-concentration effect.

Under conditions of 10 mM phosphate buffer, no polarization effect was observed in channels with a depth greater than 50 nm, probably due to the low pH (which suppressed surface ionization) or too high buffer ionic strength (where the nanofilter becomes less permselective due to smaller Debye length).

Molecules and dyes used included rGFP (BD bioscience, Palo Alto, Calif.), FITC-BSA (Sigma-Aldrich, St. Louis, Mo.), FITC-Ovalbumin (Molecular Probes, Eugene, Oreg.), FITC-BSA (Sigma-Aldrich, St. Louis, Mo.), FITC dye (Sigma-Aldrich, St. Louis, Mo.), Mito Orange (Molecular Probes, Eugene, Oreg.), and lambda-DNA (500 µg/ml). DNA molecules were labeled with YOYO-1 intercalating dyes (Molecular Probles, Eugene, Oreg.) by following manufacturer's instruction.

Also, $NH_2$-GCEHH—COOH (SEQ ID NO: 1) (pI 4.08) peptide molecules were synthesized at the Biopolymers Laboratory at the Massachusetts Institute of Technology and labeled with a thiol-conjugating dye by the following procedure: HPLC purified peptide sample was first reconstituted to a 10 mM peptide concentrated solution (0.1 M pH 7.4 phosphate buffer) as a stock solution, then diluted to 1 mM. The diluted stock solution was mixed at a 1 to 1 ratio with 10 mM TCEP (Molecular Probes, Eugene, Oreg.) and 5-TMRIA dye (Molecular Probes, Eugene, Oreg.). The reaction was allowed to proceed at 4° C. for 24 hours, shielded from exposure to light, following which, non-reacted dyes were terminated by adding 100 mM 2-Mercaptoethanol (Sigma-Aldrich, St. Louis, Mo.), and dialyzed out, using a mini-dialysis kit with 1 kDa cut-off (Amersham Bioscience, Piscataway, N.J.).

Optical Detection Setup

All the experiments were conducted on an inverted microscope (IX-71) with fluorescence excitation light source attached. A thermoelectrically cooled CCD camera (Cooke Co., Auburn Hill, Mich.) was used for fluorescence imaging. Sequences of images were analyzed by IPLab 3.6 (Scanalytics, Fairfax, Va.). A home-made voltage divider was used to distribute different potentials to reservoirs. The built in 100W mercury lamp was used as a light source, and a neutral density filter is used to reduce the light intensity and to increase the dynamic range of detection.

Quantification of Molecular Concentration

Figure 4:
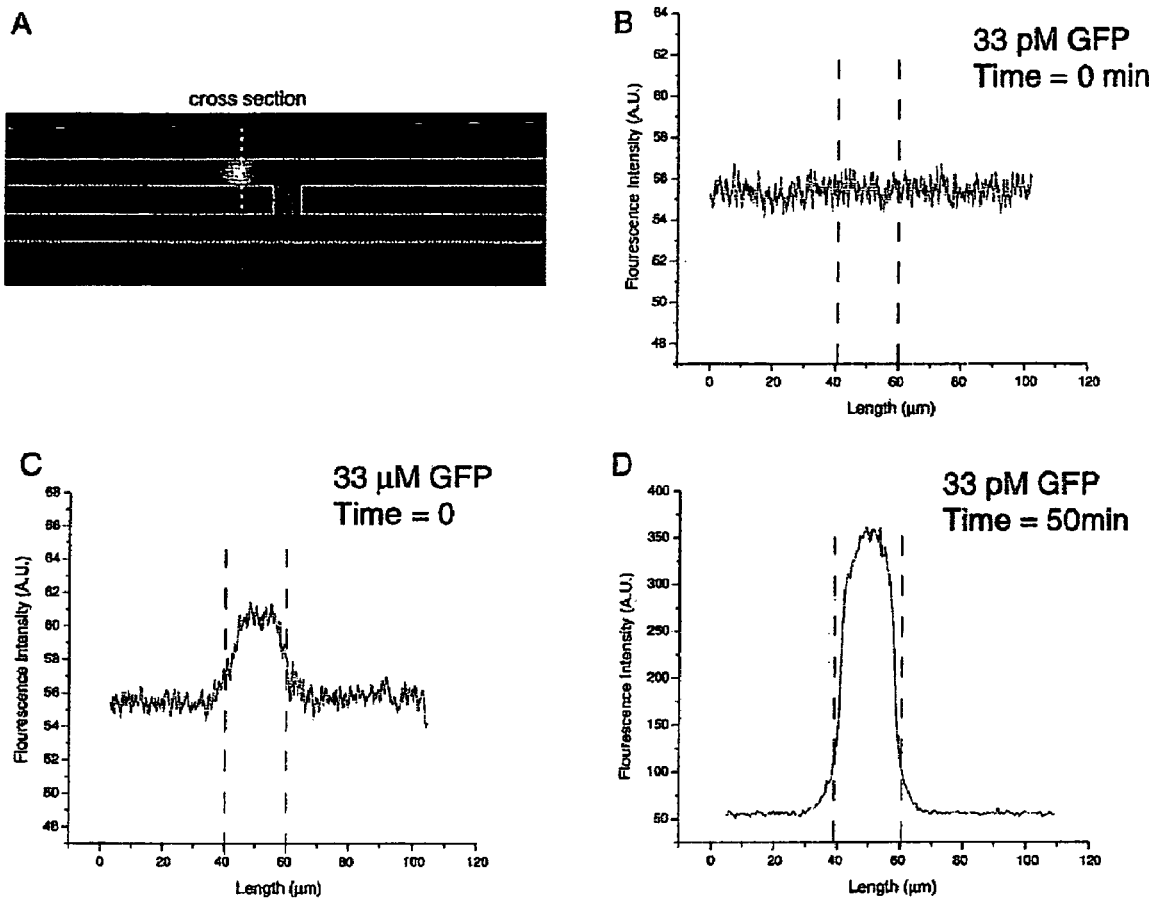
FIG. 4 is a fluorescence image of focused proteins (GFP) in the channel. (A) GFP concentration occurs near the nanofilter, the image was obtained from loading of an initial 33 pM GFP solution, after 50 mins of sample collection. The microchannel (20 µm wide, 1 µm deep) is shown by a gray line, while nanofilter is drawn by a solid block (40 nm deep). (B) Channel fluorescence signal profile at the initial concentration (33 pM GFP solution), which is below noise floor. (C) Channel fluorescence signal profile at the concentration of 0.33 µM GFP, which is barely detectable by the CCD detection setup. (D) The fluorescence signal profile of the concentrated GFP in the channel (FIG. 2(A)). The concentration of the plug is much higher than that of (C).
Figure 5:
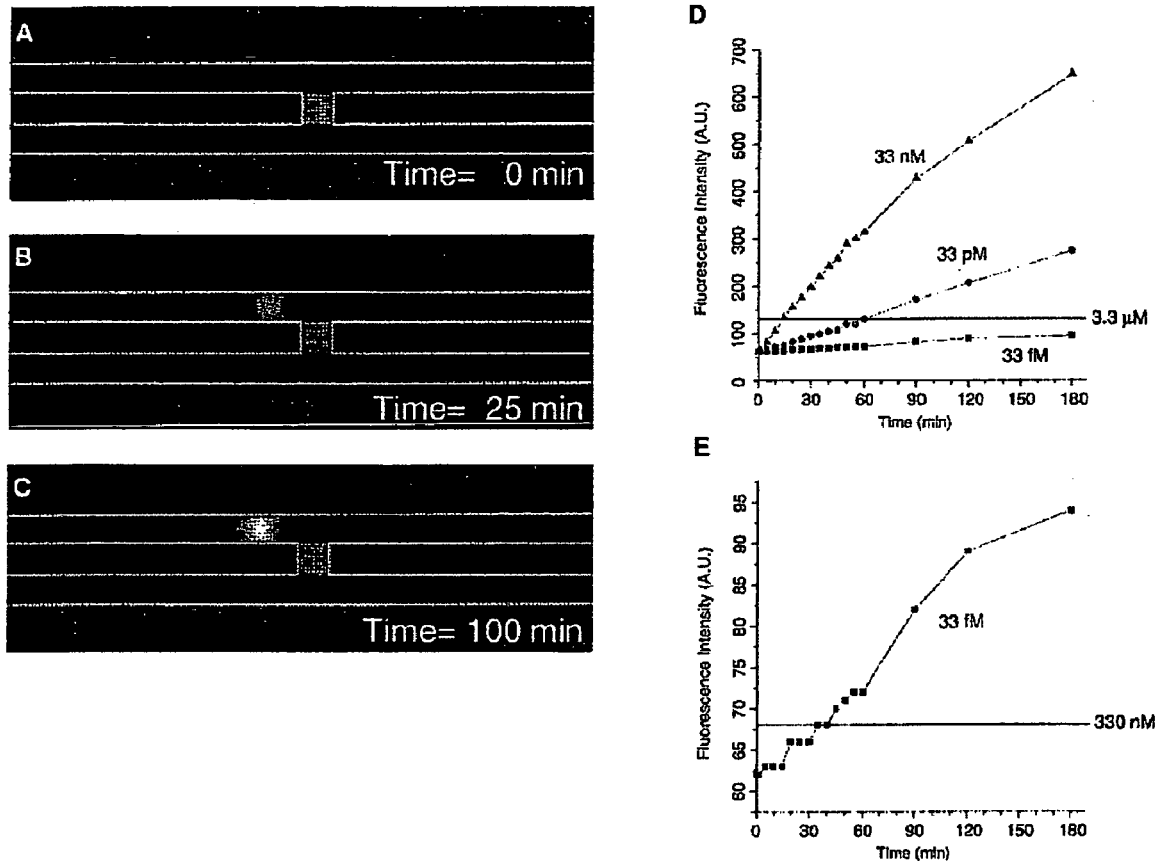
FIG. 5 demonstrates the stability and efficiency of one embodiment of the device. (A) A fluorescence image taken directly after loading a 33 pM GFP sample into the top microfluidic channel of the embodied device. (B) The image taken after applying $V_S$=10 V, $V_D$=5 V, and $V_{B1}$=$V_{B2}$=0 V for 25 mins. (C) The image taken after 100 mins with the same potential values at the reservoirs. (D) The plot of local concentration of the collected GFP plug, starting from dilute GFP solutions with three different concentrations. (E) The close-up view for 33 fM GFP experiment in (D). This shows at least $10^7$ fold concentration achieved within 40 minutes.
Figure 6:
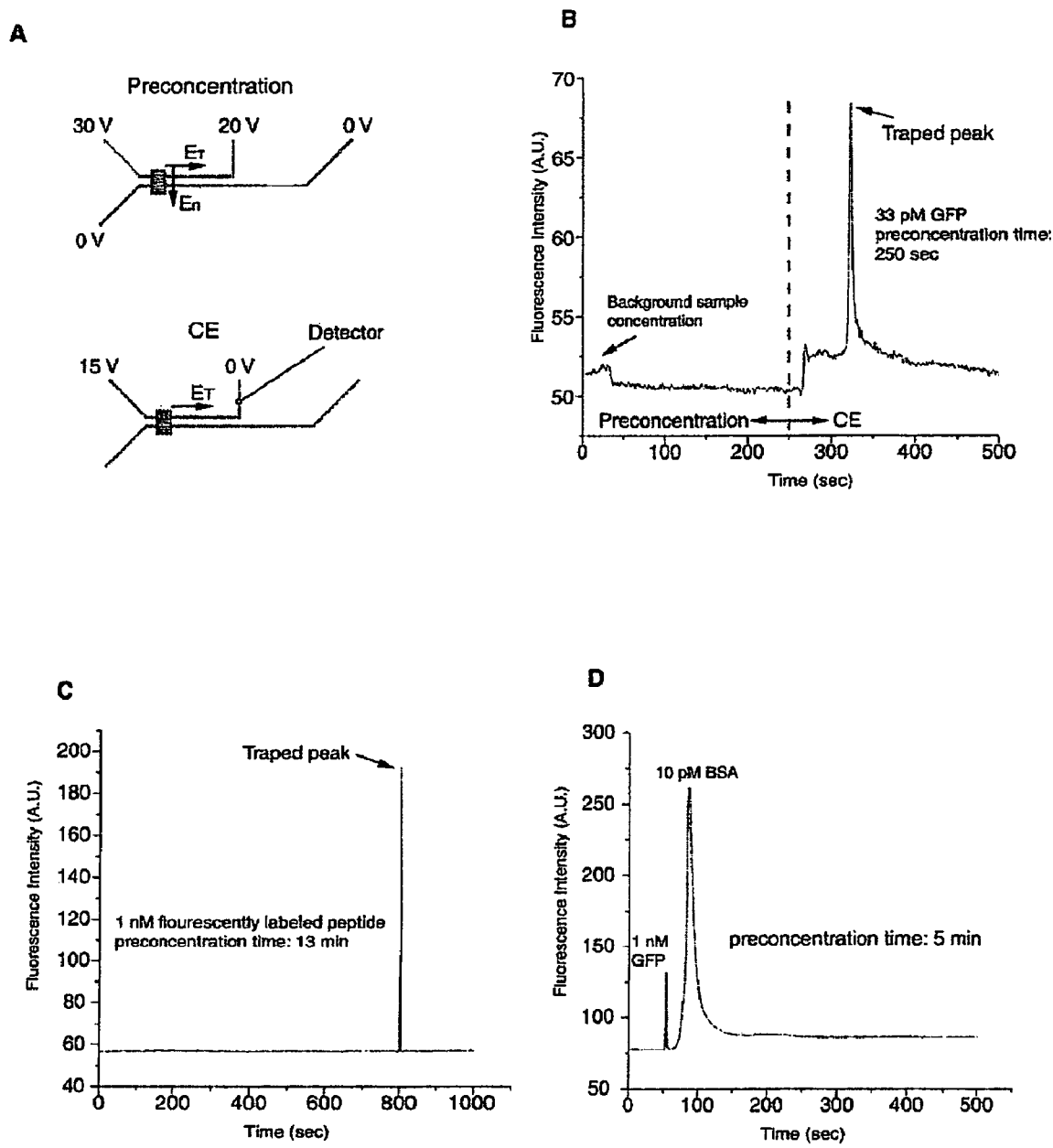
FIG. 6 demonstrates release of collected biomolecules. (A) A schematic drawing shows the voltages applied to the reservoirs during the concentrating and release (capillary electrophoresis) steps. (B) From 0 to 250 sec, the waste channel was grounded, and a voltage is applied across the filter triggering the trapping phenomena. As a result, the detector arranged downstream reads only the dark noise from the CCD array. The signal showing from 0 to 30 sec comes from 33 pM GFP solution exiting between the detector and nanofilter (about 10 mm). To show each step in greater detail, the neutral density filter was not used. Therefore, the pM level GFP sample is in the detectable range. After 250 seconds, the waste channel was floated to release the collected molecules in the top channel. (C) Collection and release of fluorescently-labeled peptide sample. An extremely sharp sample plug is formed (with more than 1000-fold preconcentration in 500 sec), which saturates the CCD array used. (D) Capillary electrophoresis separation of two different proteins, co-collected for 5 mins and released (launched).

Quantification of the molecular concentration in the channel is depicted in FIGS. 4-6. Since the device can generate sample plugs that saturate the CCD array used for detection, a neutral density filter, which allowed for at least 12% transmission (Olympus (32ND12)) was used with 70% NA aperture (50% transmission) to decrease excitation light intensity. By decreasing light intensity to 0.6%, the dynamic range of the detector was increased, while the rate of photobleaching was reduced.

Channels were filled with 3.3 µM and 0.33 µM GFP solutions, and fluorescent signal from the solutions in the channels were measured. The camera shutter was opened only during periodical exposures (~1 sec) to minimize photobleaching of the collected molecules.

In order to prevent non-specific binding of proteins, prior to and following each experiment, chips were exposed to a laser, for a period of time sufficient to completely quench residual fluorescence due to the non-specific binding of the fluorescent protein to the wall, in addition to use of freshly fabricated and filled devices, to eliminate carryover effects.

Pre-concentration in Coated Channel

In order to prevent the adsorption of samples on untreated silica surfaces, a standard polyacryamide coating (S. Hjerten, *J. Chromatogr.* 347, 191-198 (1985)) was applied. The device was coated with 3-(trimethoxysilyl)propyl methacrylate as an adhesion promoter. Then, 5% polyacrylamide solution was mixed with 0.2% VA-086 photoinitiator (WAKO, Richmond, Va.) and exposed under a UV-lamp from 5 minutes, to initiate polymerization. After the coating, there was no noticeable level of adsorption to the device. Even though the polyacryamide coating process was expected to decrease surface potential and surface charge density, similar charge polarization and sample trapping pattern was observed (albeit with a lower efficiency) by applying a higher operating potential. The lower efficiency was overcome by adopting an even lower buffer ionic strength.

Preconcentration with Diverse Buffer Conditions

To demonstrate the adaptability of the device to different buffer conditions, buffer concentrations at different pH (5-9), different buffer solutions and different ionic strengths were evaluated. The operation of the device was also tested using an extract solution that comes directly from a polyacrylamide gel slice, after performing reduction, alkylation, trypsinzation, and peptide isolation, simulating using biosamples directly from gel electrophoresis in the device, as in typical proteomics research environments. The extract solution contained no proteins, but small amounts of salts and small molecules may have been present in the gel from the sample or electrophoresis buffer (Tris, glycine, Sodium dodecyl sulfate, glycerol, Dithiothreitol, possible keratin contaminants), from staining (Coomassie blue), and/or from the reduction and alkylation steps (Tris(2-carboxy-ethyl)-phosphine hydrochloride, iodoacetamide, ammonium bicarbonate). The extraction by sonication was performed on the trypsinization solution (60 µL; 10 ng/µL trypsin and/or trypsin peptides in ammonium bicarbonate buffer) following enzyme inactivation with 20 µL of 20% formic acid. This extraction solution was collected and concentrated in the speedvac. Extraction with sonication was performed sequentially using 200 µL of 100 mM ammonium bicarbonate, 0.1% trifluoroacetic acid (TFA) in water, twice 0.1% TFA in 50:50 water to acetonitrile. Each time the extracted solution was collected and pooled with the extracted solution from the preceding step and concentrated down to approximately 10 µL in the speedvac. Then, this complex solution was used as a 'sample buffer' by adding labeled GFP molecules. For the preconcentration step, this simulated sample solution was diluted with 10 mM phosphate buffer (1:9 ratio) and loaded into the channel.

Example 1

Concentration of Charged Species Via Electroosmosis and Electrokinetic Trapping Biomolecules are efficiently concentrated in a device, which provides for a nonlinear electroosmotic flow (much stronger than normal electroosmotic flow) generated in a channel of the device, conveying biomolecules to a "trapping region" with a high flow speed, in combination with an energy barrier for the molecules generated by an induced space charge layer in the device. The combination of these two phenomena results in a rapid concentration of charged biomolecules, for example, proteins and peptides within a microfluidic channel of the device, without any physical barriers or reagents, up to $10^6$~$10^8$ fold in concentration.

One embodiment of the device is schematically depicted in FIGS. 1A and B. One or many thin nanofluidic channels (1-10), typically less than 50 nm in thickness, connect at least two microfluidic channels (1-20). Two separate electric fields are applied to the device, and controlled independently, as shown in FIG. 1B. The field in the nanofluidic channel ($E_n$) is used to generate an ion-depletion region and extended space charge layer that traps anionic biomolecules. A tangential field induced in the microfluidic channel ($E_T$), in the anodic side, generates an electroosmotic flow, conveying molecules from the reservoir (1-30) into the trapped region (1-40).

Another embodiment of the device is schematically depicted in FIG. 2. A nanofluidic channel (2-10), connects two microfluidic channels (2-20). Electric fields are applied to the device, by means of the electrodes (2-30), as shown. The field in the nanofluidic channel ($E_n$) is used to generate an ion-depletion region and extended space charge layer that traps anionic biomolecules. A tangential field induced in the microfluidic channel ($E_T$), in the anodic side, generates an electroosmotic flow, conveying molecules from the sample reservoir (2-40) into a trapped region in the microchannel. The sample reservoir contains the sample suspended or solubilized in the fluid. Other containers with buffer in contact with the microchannels are depicted in the figure (2-50), where some function as waste reservoirs, collection means, etc., as described herein.

The device may be fabricated using standard photolithography and reactive ion etching techniques, as described. The thickness and uniformity of the nanofluidic channel structure was checked by scanning electron micrograph, and the fabrication technique used, produced nanofluidic channel as thin as 20 nm, without significant deformation or collapsing of the channel (data not shown).

Nanofluidic channels (~50 nm in thickness) can support perm-selective ion current similar to what occurs in ion-exchange membranes. Within such a thin nanofluidic channel, perm-selective portion of ion currents, caused by the counterions within the Debye layer cannot be ignored, compared with the total ion current through the nanochannel. Therefore, more counterions (from the Debye layer) than co-ions will migrate across the nanochannel when an electric field is applied (FIG. 3A). This results in net transfer of charges (counterions) from the anodic side to the cathodic side, and the overall ion concentration will be decreased on the cathodic side due to a concentration polarization effect (FIG. 3B).

Ion depletion (caused by concentration polarization) near the nanofluidic channel will make the Debye layer thicker and overlap more significantly in the nanofluidic channel, which will speed up the concentration polarization. Above a certain threshold $E_n$ value, the ion transport across the channel enters a new, non-linear regime (electrokinetics of the second kind), which has been previously reported in ion-exchange membranes. In this regime (FIG. 3C), counterions are depleted from the nanofluidic channel, and an extended space charge layer (induced electrical double layer) will be formed in the bulk solution nearby, within the microfluidic channel in this case. Within this induced electrical double layer, electroneutrality is locally broken (these charges are screening the fixed surface charges within the nanochannel), and co-ions (biomolecules) are prohibited from this region because of its negative potential just as in the Debye layer.

Such an induced mobile ion layer could generate a strong electroosmotic flow when a tangential component of electric field ($E_T$) is applied (FIG. 3D). By carefully controlling the electric fields ($E_n$ and $E_T$), one can balance the two forces (anion repulsion from the space charge layer vs. nonlinear electroosmotic flow from the reservoir), stabilizing the interface. This interface is where anionic biomolecules are trapped and collected.

Nonlinear electroosmotic flow has a flow velocity, which is a nonlinear function (in this case ~$E_T E_n$) of the electric field. Much stronger electroosmotic flow velocity can be generated (typically 10~100 times faster), as compared to normal electroosmotic flow (caused by the surface Debye layer charges). Others using charged membrane beads, demonstrated the generation of electroosmosis of the second kind, however such flow produced strong but uncontrollable flow vortices near the membrane, which were used for a fast mixing. The extended space charge layer is at an unstable, non-equilibrium state, providing chaotic or oscillatory ion transport behavior in such systems.

In contrast to previous reports, electroosmosis here was well-controlled, due to the stability of the solid-state nanofluidic charge-selective interface generated, which also contributed to the efficiency of concentration.

Example 2

Protein Concentration Via Electroosmosis and Electrokinetic Trapping

FIG. 4 demonstrates a procedure used for the quantification of the molecular concentration in the channel. The embodied device can generate sample plugs that saturate the CCD array used for detection, and thus neutral density filters may be used. The concentration of collected GFP protein plugs was estimated by measuring the fluorescence signal from the molecules in the channels. Channels filled with 3.3 µM and 0.33 µM GFP solutions, allowed for little detection of the 0.33 µM GFP solution (FIG. 4C). The two intensity levels were compared with local intensity level after preconcentration of the molecules (FIG. 4D).

FIG. 5 demonstrates the stability and performance of the embodied device. In FIG. 5(A-C), a solution of 33 M GFP (green fluorescent protein) was loaded into the sample reservoir, and the resulting trapped protein peaks were monitored by fluorescence microscopy. Protein concentration was stably maintained for an extended period of time (several hours), which allowed for concentration of factors of more than a million. FIG. 5D and SE demonstrate concentration of dilute GFP protein solutions of 33 nM, 33 pM, and 33 fM monitored over a course of approximately 3 hours. Concentration of proteins in the embodied device, by factors of $10^6$~$10^8$ were achieved. The collection speed decreased when the plug concentration was high (~1 μM), probably due to the excessive non-specific binding of the protein on the channel surface.

Concentration speed in the embodied device was high. $10^7$-fold concentration was achieved within an hour. Since the approximate volume of the concentrated plug is about 0.5 pL (~1.5 μm×20 μm×20 μm), this means the embodied device pumped a sample liquid volume as large as 1 μL through the channel and trapped the GFP within that volume. Given the concentration time of ~$10^4$ sec in this experiment, the average sample flow speed should be as high as 1 mm/sec, a value not obtainable with normal electroosmotic flow (first order), which only generates up to 10~100 μm/sec with the field used in this experiment (~10V/cm). The fast collection (and fast sample fluid pumping) can be only explained by the occurrence of electroosmosis with second order kinetics. Induced space charges are generated within the microchannel by the field ($E_n$), and the tangential field ($E_T$) mobilizes these induced space charges toward the cathodic reservoir. Therefore, the preconcentrator in this paper not only traps the molecules but also pumps the sample liquid very efficiently. In addition to sample concentration, the embodied device may serve as a microfluidic pumping device, which is much more efficient than electroosmotic (electrokinetic) pumping, and simpler to implement than AC electrokinetic pumping.

Other conditions evaluated for biomolecular concentration using the embodied device include varying the ionic strength of the buffer used. While the preconcentration efficiency is improved when the ionic strength of the buffer is decreased, it can be operated even at 10 mM phosphate buffer condition.

Varying the nanofluidic channel thickness, and or buffer ionic strength or composition was evaluated as well (data not shown). In general, increasing nanofluidic channel thickness, is inversely proportional to the buffer ionic strength required for the operation of the embodied device.

Further, varying the size and number of the nanofilters in a given device affect the concentration efficiency of the device, due to different electrical field distributions in the system.

The embodied device was tested for its ability to concentrate proteins (FIG. 4), synthesized peptide (FIG. 5), fluorescent dye, and fluorescent beads in solution (data not shown). Further, device operation was tested when the device surface was coated with polyacrylamide polymer to prevent non-specific binding of the biomolecules. In all cases, molecular trapping was accomplished, with concentration speed varying as a function of the different conditions applied.

This clearly demonstrates the flexibility and adaptability of the device toward further integration. Even a complex solution directly from the in-gel digestion of gel electrophoresis (which has high-ionic strength and contains some organic solvents) can be used, after being diluted in the phosphate buffer of 10 mM. This opens up the possibility of using samples directly from gel electrophoresis or other conventional purification techniques (using high ionic strength buffers) in the preconcentration device.

Example 3

Analysis of Proteins Concentrated Via Electroosmosis and Electrokinetic Trapping Molecular trapping in the embodied device can be turned off by removing $E_n$. The buffer solution is expected to re-establish the ionic balance as soon as the field is turned off. When the field is turned off, the collected peak is instantly dispersed to about twice the original peak width, but there is no further dispersion observed. Therefore, the molecular plug generated by the embodied device can be easily manipulated either by electric field (electrophoresis) or pressure-driven flow. FIG. 6 demonstrates capillary electrophoresis of two protein species collected by the embodied device. The results indicate effective coupling of the embodied device and downstream analysis tools, in this case, free solution capillary electrophoresis.

Example 4

Manipulation of Buffer Conditions Increases Stability of Space Charge Region

It is possible to further stabilize the space charge region by manipulating buffer conditions in the devices of the invention (FIG. 7). In one embodiment, a device comprising two or a series of two microchannels are each connected by a nanochannel. According to this embodiment, over a course of time, ion depletion in a top microchannel (7-10) leads to ion enrichment in a bottom microchannel (7-20), thus the buffer concentration in the bottom microfluidic channel increases with prolonged conduction of the separation process. In one embodiment, the section closest to the nanochannel (7-30), in particular, is affected. With time, the ion selectivity of the nanofluidic channel may weaken and unstable depletion in the top channel may result. It is possible, however, to provide a source of a lower concentration of the buffer, at prescribed time periods, in one embodiment, or continually, in another embodiment, by electroosmosis, or in another embodiment, by pressure driven flow.

Example 5

Specific Orientation of the Channels Can Increase Stability of the Space Charge Region In another embodiment of the invention, preconcentration of the material may be enhanced by positioning nanofluidic channels (8-10) on both sides of the microchannel (8-20), and in fluid communication with the microchannel (FIG. 8). Because ion depletion initiates at the interface between the microchannel and the nanochannel, when only one nanochannel is present adjacent to the microchannel, ion depletion must extend across the entire length of the microfluidic channel, before separation can occur. As shown in FIG. 8, positioning of nanochannels on either side of the microchannel, allows for faster and more complete ion depletion (8-30), and in some embodiments, a more stable space charge region.

What is claimed is:
1. A concentrating device comprising:
   at least one microchannel, wherein said microchannel fluidically connects a first fluid reservoir and a second reservoir, and a second end;
   at least one nanochannel, wherein said nanochannel fluidically connects to said first and said second fluid reservoir by a microchannel and is fluidically connected to at least one additional fluid reservoir;
   a unit to induce an electric field from said microchannel across said nanochannel by applying a voltage between either a first or second fluid reservoir and at least one said additional fluid reservoir such that an ion depletion zone is formed within said microchannel, which provides an energy barrier to a species of interest;

a unit to induce an electric field across said microchannel by applying a voltage between said first and second fluid reservoir; and a unit to induce an electrokinetic flow or pressure driven flow across said microchannel; and a conduit, through which a liquid comprising said species of interest can be made to pass;

wherein said microchannel is linked to said nanochannel, and said conduit is linked to said microchannel.

2. The device of claim 1, whereby upon introduction of a liquid comprising said species of interest in said device and independent induction of said electric field from said microchannel across said nanochannel and induction of said electric field across said microchannel and induction of said electrokinetic flow or said pressure driven flow or a combination thereof across said microchannel, said species of interest is concentrated within said microchannel.

3. The device of claim 1, wherein said unit to induce an electric field from said microchannel across said nanochannel and said unit to induce an electric field across said microchannel are a voltage supply.

4. The device of claim 3, wherein said voltage applied by said voltage supply is between 50 mV and 500 V.

5. The device of claim 3, wherein said voltage supply applies equal voltage to two sides of said microchannel.

6. The device of claim 3, wherein said voltage supply applies greater voltage to the anodic side of said microchannel, as compared to the cathodic side.

7. The device of claim 1, wherein the width of said microchannel is between 1-100 μm.

8. The device of claim 1, wherein the depth of said microchannel is between 0.5-50 μm.

9. The device of claim 1, wherein the width of said nanochannel is between 1 μm-50 μm.

10. The device of claim 1, wherein the depth of said nanochannel is between 20-100 nanometers.

11. The device of claim 1, wherein the surface of the microchannel has been functionalized to reduce or enhance adsorption of said species of interest to said surface.

12. The device of claim 1, wherein the surface of the nanochannel and/or microchannel has been functionalized to enhance or reduce the operation efficiency of the device.

13. The device of claim 1, wherein an external gate potential is applied to the substrate of the device, to enhance or reduce the operation efficiency of the device.

14. The device of claim 1, wherein said microchannel or nanochannel or combination thereof, are formed in said device by a lithography and etching processes.

15. The device of claim 1, wherein said device is comprised of a transparent material.

16. The device of claim 13, wherein said transparent material is pyrex, silicon dioxide, silicon nitride, quartz or SU-8.

17. The device of claim 1, wherein said device is coated with a low-autofluorescent material.

18. The device of claim 1, wherein said device is coupled to a separation system, detection system, analysis system or combination thereof 19. The device of claim 1, wherein said device is coupled to an illumination source.

20. The device of claim 1, wherein said device comprises multiple microchannels, nanochannels or combinations thereof.

21. The device of claim 20, wherein said multiple microchannels, nanochannels or combinations thereof are arranged with a particular geometry.

22. The device of claim 21, wherein said geometry comprises perpendicular orientation of said microchannels with respect to said nanochannels.

23. The device of claim 22, wherein each microchannel is linked to two nanochannels, which are oriented perpendicularly with respect to said microchannel.

24. The device of claim 20, wherein said device comprise a first and a second microchannel each linked to a nanochannel, wherein a sample is loaded in a buffered suspension or solution in said first microchannel and a lower concentration of said buffered suspension or solution is loaded in said second microchannel.

25. A microfluidic pump comprising the device of claim 1.

26. The pump of claim 25, wherein said pump has a liquid flow speed of between 10 μm/sec and 10 mm/sec.

27. A method comprising the use of the device of claim 1 in concentrating a species of interest in a liquid.

28. A method of concentrating a species of interest in a liquid, the method comprising the steps of:

introducing liquid from a source into a concentrating device, wherein said liquid comprises a species of interest and wherein said device comprises a microchannel, wherein said microchannel fluidically connects a first fluid reservoir and a second fluid reservoir, and a second end, linked to a nanochannel, wherein said nanochannel fluidically connects to said first and said second fluid reservoir by a microchannel and is fluidically connected to at least one additional fluid reservoir;

inducing an electric field from said microchannel across said nanochannel, by applying a voltage between either a first or second fluid reservoir and at least one said additional fluid reservoir, whereby ion depletion occurs in a region wherein said microchannel is linked to said nanochannel, and an ion depletion zone is formed within said microchannel, which provides an energy barrier to said species of interest; and inducing an electric field across said microchannel by applying a voltage between said first and second fluid reservoir such that said species of interest is concentrated within said microchannel; and inducing electrokinetic flow or pressure driven flow or a combination thereof across said microchannel, such that said species of interest is concentrated within said microchannel.

29. The method of claim 28, wherein said flow is electroosmotic.

30. The method of claim 29, wherein said electroosmotic flow is induced in said microchannel via said induction of an electric field across said microchannel.

31. The method of claim 28, wherein said flow is pressure driven.

32. The method of claim 28, wherein steps are carried out cyclically.

33. The method of claim 28, wherein an electric field is induced in said nanochannel, said microchannel, or a combination thereof.

34. The method of claim 28, wherein said electric field induced across said nanochannel, or across said microchannel, or combination thereof, is via applying voltage to said nanochannel, microchannel, or combination thereof.

35. The method of claim 28, wherein at least one microchannel is linked to at least one nanochannel, and is oriented perpendicularly with respect to said nanochannel.

36. The method of claim 35, wherein each microchannel is linked to two nanochannels, which are oriented perpendicularly with respect to said microchannel.

37. The method of claim 28, wherein a first and a second microchannel are each linked to a nanochannel, wherein a sample is loaded in a buffered suspension or solution in said first microchannel and a lower concentration of said buffered suspension or solution is loaded in said second microchannel.

38. The method of claim 34, wherein said voltage is between 50 mV and 500 V.

39. The method of claim 34, wherein equal voltage is applied to the two sides of said microchannel.

40. The method of claim 34, wherein greater voltage is applied to the anodic side of said microchannel, as compared to the cathodic side.

41. The method of claim 40, wherein an ion depletion zone is generated in said microchannel prior to applying said greater voltage to said anodic side of said microchannel.

42. The method of claim 28, wherein the width of said microchannel is between 1-100 μm.

43. The method of claim 28, wherein the the depth of said microchannel is between 0.5-50 μm.

44. The method of claim 28, wherein the width of said nanochannel is between 1 μm-50 μm.

45. The method of claim 28, wherein the depth of said nanochannel is between 20-100 nanometers.

46. The method of claim 28, wherein the surface of the microchannel has been functionalized to reduce or enhance adsorption of said species of interest to said surface.

47. The method of claim 28, wherein the surface of the nanochannel and/or microchannel has been functionalized to enhance or reduce the operation efficiency of the device.

48. The method of claim 28, wherein an external gate potential is applied to the substrate of the device, to enhance or reduce the operation efficiency of the device.

49. The method of claim 28, wherein said microchannel or nanochannel or combination thereof, are formed in said device by a lithography and etching processes.

50. The method of claim 28, wherein said liquid is a suspension or solution.

51. The method of claim 50, wherein said suspension is an organ homogenate, cell extract or blood sample.

52. The method of claim 28, wherein said species of interest comprises proteins, polypeptides, nucleic acids, viral particles, or combinations thereof.

53. The method of claim 28, wherein said device is comprised of a transparent material.

54. The method of claim 28, wherein said transparent material is pyrex, silicon dioxide, silicon nitride, quartz or SU-8.

55. The method of claim 28, wherein said device is coated with a low-autofluorescent material.

56. The method of claim 28, wherein said device is coupled to a separation system, detection system, analysis system or combination thereof.

57. The method of claim 28, wherein said device is coupled to an illumination source.

58. The method of claim 28, further comprising the step of subjecting said species of interest to capillary electrophoresis.

59. The method of claim 28, further comprising the step of releasing said species of interest from said device.

60. The method of claim 28, wherein said method is utilized to detect said species of interest when said species is present in said liquid at a concentration which is below a limit of detection.

61. A method for controlling liquid flow in a system, the method comprising:

applying said liquid from a source to a pumping device in said system, wherein said device comprises a microchannel, wherein said microchannel fluidically connects a first fluid reservoir and a second fluid reservoir, and a second end, linked to a nanochannel, wherein said nanochannel fluidically connects to said first and said second fluid reservoir by a microchannel and is fluidically connected to at least one additional fluid reservoir; and said liquid comprises a charged species or an amphoteric species;

inducing an electric field from said microchannel across said nanochannel, by applying a voltage between either a first or second fluid reservoir and at least one said additional fluid reservoir, whereby ion depletion occurs in a region wherein said microchannel is linked to said nanochannel, and an ion depletion zone is formed within said microchannel, which provides an energy barrier for said species of interest; and inducing an electric field across said microchannel by applying a voltage between said first and second fluid reservoir whereby electroosmotic flow is induced in said microchannel, said flow further introducing said liquid into said device and said flow is controlled by the strength of said electric field.

62. The method of claim 61, wherein an electric field is induced in said nanochannel, said microchannel, or a combination thereof.

63. The method of claim 62, wherein said electric field induced in said nanochannel, or in said microchannel, or combination thereof, is via applying voltage to said nanochannel, microchannel, or combination thereof.

64. The method of claim 63, wherein said voltage is between 50 mV and 500 V.

65. The method of claim 63, wherein equal voltage is applied to the anodic and cathodic side of said microchannel.

66. The method of claim 63, wherein greater voltage is applied to the anodic side of said microchannel, as compared to the cathodic side.

67. The method of claim 66, wherein an ion depletion zone is generated in said microchannel prior to applying said greater voltage to said anodic side of said microchannel.

68. The method of claim 61, wherein the width of said microchannel is between 1-100 μm.

69. The method of claim 61, wherein the depth of said microchannel is between 0.5-50 μm.

70. The method of claim 61, wherein the width of said nanochannel is between 1 μm-50 μm.

71. The method of claim 61, wherein the depth of said nanochannel is between 20-100 nanometers.

72. The method of claim 61, wherein said electroosmotic flow has a rate of between 500 μm/sec to 1 mm/sec.

73. The device of claim 3, wherein said voltage applied by said voltage supply from said microchannel across said nanochannel comprises applying a positive voltage to at least one side of said microchannel, and electrically grounding the end of said nanochannel which is farthest from said microchannel.

74. The method of claim 34, wherein said voltage applied from said microchannel across said nanochannel comprise applying a positive voltage to at least one side of said microchannel, and electrically grounding the end of said nanochannel which is farthest from said microchannel.

\* \* \* \* \*

UNITED STATES PATENT AND TRADEMARK OFFICE
CERTIFICATE OF CORRECTION

PATENT NO. : 7,651,600 B2 Page 1 of 1
APPLICATION NO. : 11/338885
DATED : January 26, 2010
INVENTOR(S) : Han et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 522 days.

Signed and Sealed this

Twenty-third Day of November, 2010

David J. Kappos
*Director of the United States Patent and Trademark Office*